United States Patent [19]

Christopherson et al.

[11] Patent Number: 4,636,204
[45] Date of Patent: Jan. 13, 1987

[54] COUPLING FOR THE CONNECTION OF FLEXIBLE TUBES AND THE LIKE

[75] Inventors: Kjell H. Christopherson; Tomas Odelius, both of Staffanstorp, Sweden; Friedrich Rosemeier, Hechingen, Fed. Rep. of Germany; Kaj O. Stenberg, Staffanstorp; Tommy E. Svensson, Lund, both of Sweden; Horst Killmaier, Hechingen-Boll, Fed. Rep. of Germany

[73] Assignee: Gambro Lundia AB, Sweden

[21] Appl. No.: 742,148

[22] Filed: Jun. 7, 1985

Related U.S. Application Data

[63] Continuation of Ser. No. 484,197, Apr. 12, 1983, abandoned.

[30] Foreign Application Priority Data

Apr. 13, 1982 [SE] Sweden .................. 8202290

[51] Int. Cl.⁴ .............................................. A61M 25/00
[52] U.S. Cl. ...................... 604/283; 604/411; 604/415; 604/905
[58] Field of Search ............. 604/206, 905, 411, 415, 604/408, 283

[56] References Cited

U.S. PATENT DOCUMENTS

| | | | |
|---|---|---|---|
| 3,766,919 | 10/1973 | Cloyd | 604/206 X |
| 3,838,843 | 10/1974 | Bernhard | 251/149.1 |
| 3,915,212 | 10/1975 | Bujan et al. | 604/415 X |
| 3,986,508 | 10/1976 | Barrington | 285/3 X |
| 4,161,949 | 7/1979 | Thanawalla | 604/905 X |
| 4,294,250 | 10/1981 | Dennehey | 604/283 |
| 4,432,764 | 2/1984 | Lopez | 604/905 X |
| 4,439,188 | 3/1984 | Dennehey et al. | 604/283 |

FOREIGN PATENT DOCUMENTS

| | | | |
|---|---|---|---|
| 81/00053 | 1/1981 | PCT Int'l Appl. | 604/905 |
| 2067075 | 7/1981 | United Kingdom | 604/905 |

Primary Examiner—Michael H. Thaler
Attorney, Agent, or Firm—Lerner, David, Littenberg, Krumholz & Mentlik

[57] ABSTRACT

A coupling member is disclosed for use in connecting together flexible tubes and the like. The coupling member is adapted for connection with a mating coupling member, and includes an outer rigid coupling component which is thermally resistant and an inner coupling component which is thin and flexible, so that the inner coupling component can provide a penetrable seal and whereby the overall coupling member is capable of withstanding autoclaving temperatures so that it can be sterilized prior to use. A coupling device including such a coupling member is also disclosed, including a second coupling member which is capable of mating with the first coupling member and which includes a penetrating portion so that when the two coupling members are mated, the penetrating portion of the second coupling member penetrates the inner coupling component of the first coupling member. The disclosed coupling device is primarily intended for use in connection with a treatment method known as CAPD (Continuous Ambulatory Peritoneal Dialysis).

39 Claims, 6 Drawing Figures

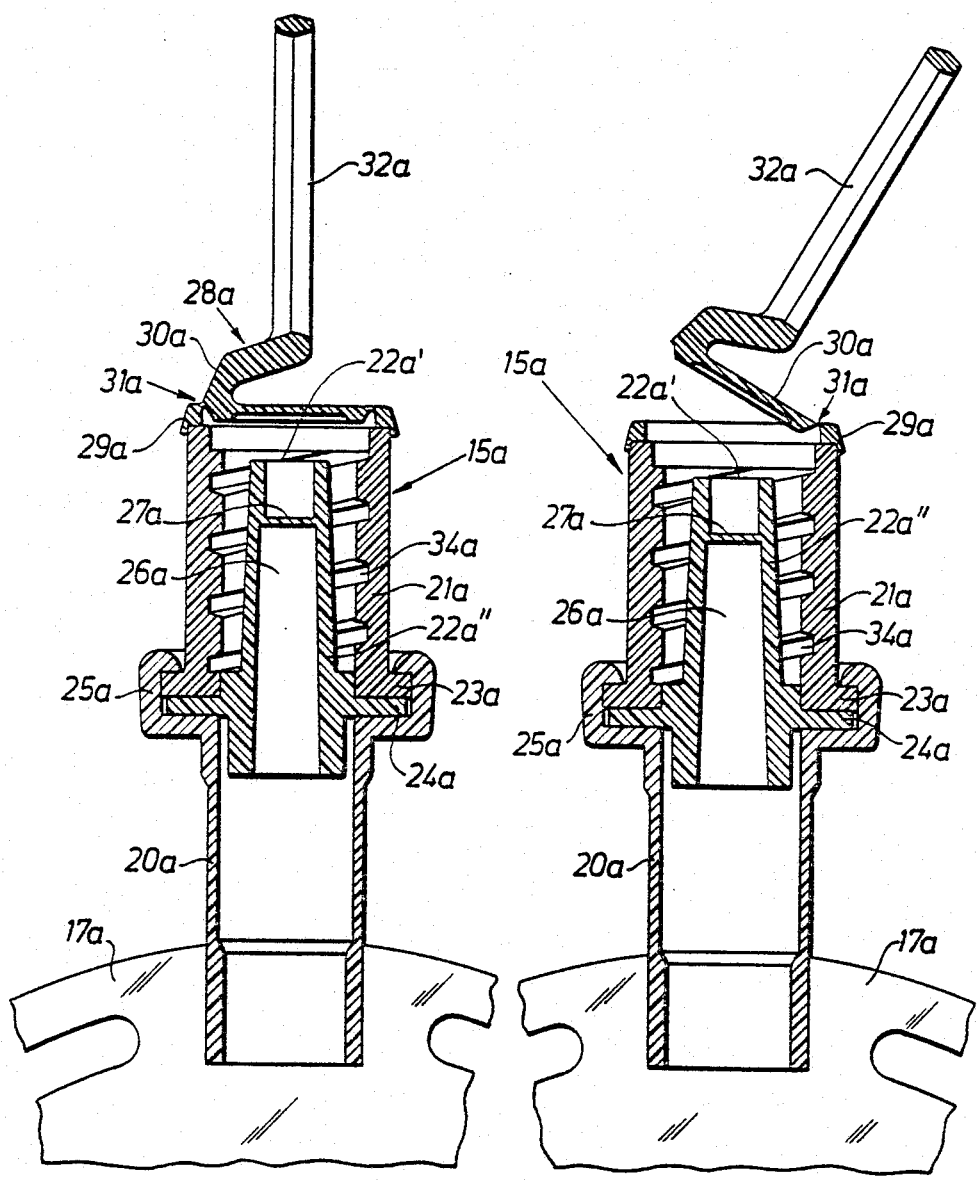

COUPLING FOR THE CONNECTION OF FLEXIBLE TUBES AND THE LIKE

This is a continuation of application Ser. No. 484,197 filed on Apr. 12, 1983, abandoned.

FIELD OF THE INVENTION

The present invention is directed to couplings, including two mating coupling pieces for the connection of flexible tubes and the like. More particularly, the present invention is directed to couplings intended for the substantially sterile joining together of two medical components, such as for example the joining together of a catheter with a flexible tube, or a bag provided with a flexible tube.

BACKGROUND OF THE INVENTION

Couplings have previously been know for use in connection with various medical treatments, e.g. the extracorporeal treatment of blood or other body fluids. The coupling of the present invention is primarily intended, however, to be used in conjunction with a method of treatment know as CAPD (Continuous Ambulatory Peritoneal Dialysis). In this method of treatment, a catheter is introduced into the patients' abdominal cavity, and projects as such or via a flexible tube through the abdominal wall. This flexible tube can then be connected by a coupling to a second flexible tube joined to a fluid bag. The coupling should thus consist of two coupling pieces or members, which are joined to the respective flexible tubes, or possibly directly to the bag itself and/or to the catheter. The first time such a coupling is used, there is normally no problem, since both coupling pieces can be supplied in a sterilized condition. After such first usage, however, when the fluid bag is to be replaced by a new one, at least one of the coupling pieces, i.e., the one connected to the abdominal catheter, may be contaminated by external impurities. It will be readily understood by those skilled in this art that this may give rise to various complications.

The couplings which are presently used for these purposes are primarily based on the principle that the patient should not be able to touch the inner parts of the coupling with his fingers. In this way, it should be possible to keep them sterile. However, a serious risk of contamination still exists if the outer components of the coupling are polluted or contaminated.

SUMMARY OF THE INVENTION

In accordance with the present invention it has now been discovered that a coupling can be provided in which at least one of the coupling members is composed of one or more components of differing rigidity, and which as a whole can withstand autoclaving. This can insure that at least the exchangeable coupling member can be supplied to the patient, in for example CAPD, and in a completely sterile condition subsequent to autoclaving. Additionally, as will become evident from the following disclosure, a number of additional advantages are obtained in connection with the handling of this coupling device.

For the sake of simplicity, the various advantages of the device of the present invention will be described in conjunction with its application to CAPD. It will become clear to those skilled in this art, however, that essentially those same advantages can be obtained in other kinds of couplings where it is desirable to avoid contamination of the coupling members so utilized.

In a preferred embodiment of the coupling of the present invention, one of the coupling members is designed to include an outer component of a material which is so rigid and thermally resistant that it is able to withstand autoclaving without any dimensional alteration affecting its essential function, and an inner component which is provided with a membrane of a less rigid material which, on joining, can be readily penetrated by a sharp component from the second or mating coupling member. In view of this construction, the less rigid component can also retain its dimensions during autoclaving.

In accordance with the coupling member of the present invention, the coupling member includes a first end, a second end, and a connecting passageway therebetween, the first end being adapted for connection with a mating coupling member, the coupling member including an outer rigid coupling component which is thermally resistant, and an inner coupling component which is thin and flexible, so that the inner coupling component is capable of providing a penetrable seal for the connecting passageway, and the coupling member itself is capable of withstanding autoclaving so that it can be sterilized prior to use.

In accordance with a preferred embodiment of the coupling member of the present invention, the inner flexible coupling component includes a membrane which separates the first and second ends of that coupling member.

In accordance with another embodiment of the coupling member of the present invention, the first end of the coupling member includes a lid member closing the outer rigid coupling component, the lid member including an area of weakness dividing it into first and second portions whereby the first portion of the lid member may be readily removed from the coupling member by tearing along the area of weakness so as to expose the first end of the coupling member for mating connection with the mating coupling member.

In accordance with a preferred embodiment of the coupling member of the present invention, the outer rigid coupling component and the inner flexible coupling component are substantially concentric, the inner flexible coupling component including a central passageway blocked by the membrane. Preferably, the inner flexible coupling component includes a first end coinciding with the first end of the coupling member and a second end coinciding with the second end of the coupling member, the first end being recessed within the first end of the coupling member, whereby the inner flexible coupling component is protected from inadvertent contact thereby. More preferably, the outer rigid coupling component and the inner flexible coupling component include peripheral flanges, so that they can be joined together at these corresponding peripheral flanges. Preferably, both of the peripheral flanges are disposed substantially perpendicular to the longitudinal axis of the coupling member, and include substantially identical outside diameters. Most preferably both of the peripheral flanges include corresponding planar faces in contact with each other, and an outer joining member is provided so as to enclose the outer diameters of both peripheral flanges.

In accordance with another embodiment of the coupling member of the present invention, the outer rigid coupling component is cylindrical and includes an interior threaded portion for threaded engagement with the mating coupling member.

In accordance with another embodiment of the coupling member of the present invention, the membrane substantially encloses the connecting passageway, so that the second end of the coupling member is sealed thereby. The membrane is preferably sufficiently thin so that steam can diffuse through the membrane during autoclaving. Preferably, the coupling member includes an annular space between the concentric inner and outer coupling components, and a second membrane portion is provided separating the central passageway from that annular space. Preferably, the second membrane comprises a plurality of second membrane portions.

In accordance with the coupling device of the present invention, first and second coupling members are provided which are capable of mating engagement with each other. The first coupling member comprises the coupling member described above, and the second coupling member includes first and second ends and a penetrating portion, so that when the two coupling members are mated together, the penetrating portion of the second coupling member penetrates the inner coupling component of the first coupling member.

In accordance with a preferred embodiment of the coupling device of the present invention, the second end of the first coupling member is integral with a flexible bag.

In accordance with another embodiment of the coupling device of the present invention, the inner flexible coupling component of the first coupling member includes a membrane separating its ends, and preferably the outer rigid coupling component and the inner flexible coupling component are substantially concentric, with the inner flexible coupling component including a central passageway blocked by the membrane. Preferably, the first end of the inner flexible coupling component is recesed within the first end of the first coupling member, so that the inner flexible coupling component is protected from inadvertent contact thereby.

In accordance with a preferred embodiment of the coupling device of the present invention, the outer rigid coupling component and the inner flexible coupling component of the first coupling member each include the aforementioned peripheral flanges.

In accordance with a preferred embodiment of the coupling device of the present invention, the outer rigid coupling component of the first coupling member is cylindrical, and the first end of the first coupling member includes an interior threaded portion, while the second coupling member is also cylindrical, and the first end of the second coupling member includes an exterior threaded portion adapted for theaded engagement with the interior threaded portion of the first coupling member. Preferably, the penetrating portion of the second coupling member is concentrically disposed within the cylindrical exterior threaded portion of the second coupling member, and is recessed with respect to the first end of the second coupling member, whereby the penetrating portion is protected from inadvertent contact during use.

In accordance with a preferred embodiment of the coupling device of the present invention, the outer rigid coupling component and the inner flexible coupling component are substantially concentric, the inner flexible coupling component including a central passageway blocked by the membrane. Preferably, the penetrating portion of the second coupling member is adapted to sealingly engage the inner flexible coupling component of the first coupling member prior to actually penetrating the membrane.

In a preferred embodiment hereof, one of the coupling pieces or members includes an opening made of such a rigid and thermally resistant material that it withstands autoclaving without any dimensional alteration affecting its essential function, and includes a lid closing that opening and made of a less rigid and readily tearable material provided with a tearing indication, so as to make it possible for a part of that lid to be torn off prior to joining together the two coupling pieces. This provides the added advantage that the less rigid part can be manufactured from a type of material which would otherwise not withstand autoclaving.

In accordance with this invention, should any parts of the coupling be contaminated, the danger of spreading of that contamination is reduced where the membrane-penetrating portion of the second coupling member is adapted to engage the first coupling member in a tight sealing manner before the membrane is actually penetrated.

The components of different rigidity are preferably in such positive engagement with one another that the mutual turning on coupling together, or possible tearing off of any part, is prevented.

To ensure tightness still further, the less rigid and readily tearable material which closes the opening may be adapted to substantially enclose the whole of the coupling piece to which it belongs, so that it forms a tight seal, at least with respect to the flexible tube, pipe or the like of which the coupling piece is intended to form an end piece.

To ensure effective autoclaving, the membrane may be of a thickness which is such that steam can effectively diffuse through it during such autoclaving. In this manner, sterilization even of any completely closed spaces on either side of the membrane is assured, since the steam now has access to that other side.

The coupling may also be provided with one or more auxiliary membranes which are not intended to be mechanically penetrated, but which are intended to supply steam to spaces which are otherwise closed during autoclaving.

BRIEF DESCRIPTION OF THE DRAWINGS

The present invention may be more fully understood with reference to the following drawings and detailed description thereof, in which:

FIG. 2 is a side, elevational, partly sectional view of a coupling member in accordance with the present invention, in a closed condition;

FIG. 3 is a side, elevational, partly sectional view of the coupling member of FIG. 2, in a partly open condition;

DETAILED DESCRIPTION

Figure 1:
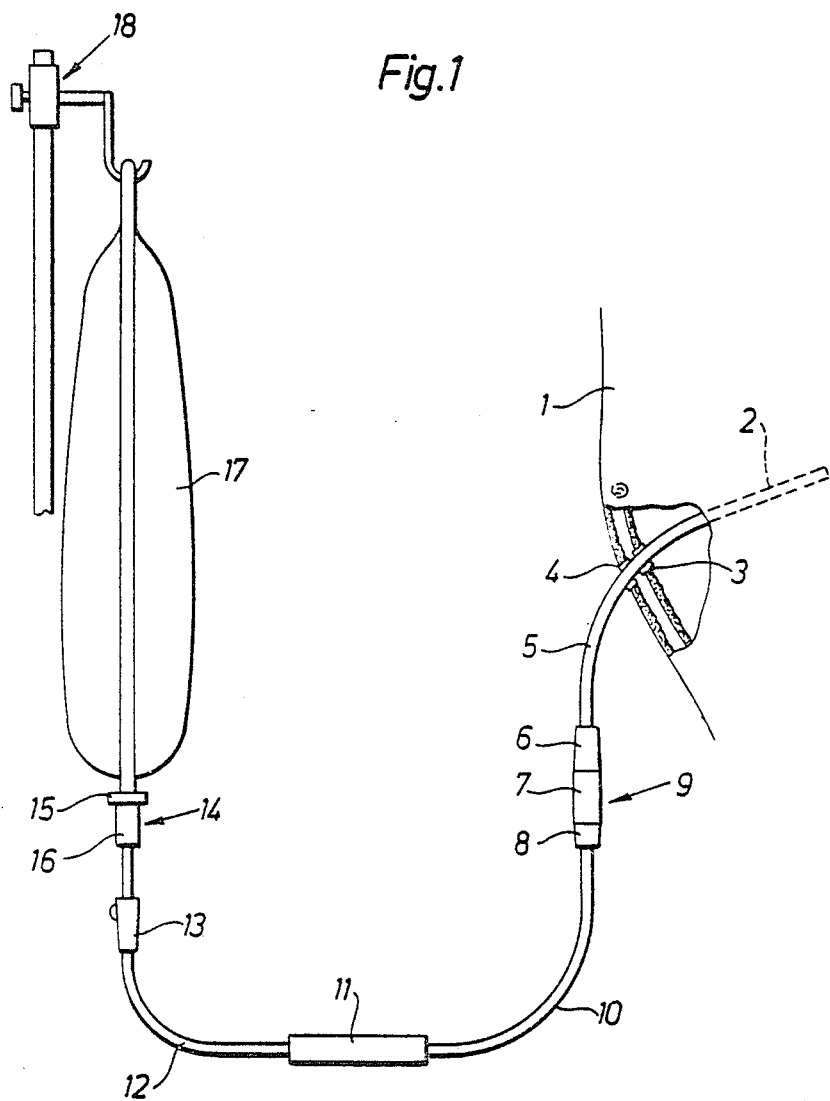
FIG. 1 is a side, elevational, partly sectional, schematic representation of the coupling of the present invention, used in a CAPD system.

Referring to the figures, in which like numerals refer to like portions thereof, FIG. 1 schematically shows a CAPD system. Referring specifically to FIG. 1, reference numeral 1 is intended to designate the patient, who has a catheter 2 introduced into his abdomen by operation. The catheter 2, by means of two seals 3 and 4, passes into an outer flexible tube 5. This tude 5 is terminated by a coupling piece 6 which, together with two coupling pieces 7 and 8, forms a coupling 9, which is only intended to be opened infrequently. The coupling piece 8 is connected to a filter 11 via a flexible tube 10. A further flexible tube 12 then connects filter 11 with a tube clip 13 and then to a coupling 14, which is the actual subject of the present invention. By means of this coupling 14, which consists of a first coupling member 15 and a second coupling member 16, a bag 17 filled with CAPD solution can be coupled to the catheter 2 for filling the peritoneal cavity in the patients' abdomen. In the example shown, the bag 17 is suspended on a simple stand 18.

The CAPD treatment thus consists of introduction of the fluid from the bag 17 into the peritoneal cavity, where it is retained for a number of hours, after which it is emptied out into the empty bag, together with any toxicant which it was intended to remove from the patient. After emptying, the bag 17 is uncoupled, along with coupling member 15, whereupon a new bag, with a new coupling member 15, can be coupled thereto for repetition of such treatment.

Referring next to FIG. 2, one embodiment of a coupling member of the coupling device of this invention is shown therein. The top portion of a CAPD bag, designated as 17a, is provided with an emptying nozzle 20a which may be said to constitute part of a coupling piece or member referred to in its entirety by numeral 15a. This coupling member 15a includes an outer cylindrical component 21a of a more rigid material, and an inner, likewise cylindrical component, 22a, of a less rigid material. These two portions are provided with peripheral flanges 23a and 24a, respectively, which are preferably welded together, as well as being enclosed by an outer, widened portion 25a of the flexible tube, i.e., in this case the emptying nozzle 20a, of which this coupling member is intended to form an end piece. In such a device, these different components thus do not have to be manufactured from a material which is mutually weldable. However, the use of such a material is preferred, so that further tightness can be insured by such welding.

The passage 26a of the inner component 22a adjacent to its opening 22a is blocked by a membrane 27a, which can be readily penetrated by a sharp object, since the whole of the inner component 22a is made up of a relatively non-rigid material.

At its end, this coupling member is terminated by a lid component 28a, which closes the opening of component 21a, and which consists of a ring 29a welded to component 21a and a tear-off portion 30a, which is attached to ring 29a via tearing indication 31a. The tearing is facilitated by means of a pull-ring 32a or the like.

Figure 4:
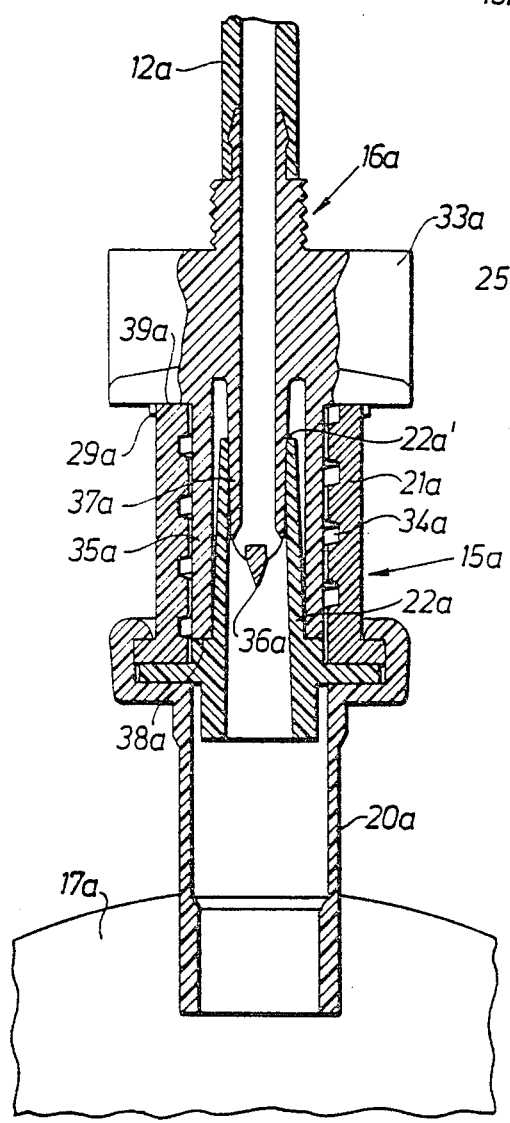
FIG. 4 is a side, elevational, partly sectional view of a portion of the coupling member of FIG. 2 mated with a second coupling member.

Referring to FIG. 3, the same coupling piece is shown partly opened, and in FIG. 4 the same coupling piece is shown joined to a second coupling piece, which is referred to in its entirety by reference numeral 16a. This coupling piece 16a is arranged as an end piece or an end portion on a flexible tube 12a. With the help of a finger grip 33a, and an internal thread 34a on component 21a, together with an external thread or partial thread (not shown) on its cylindrical portion 35a, coupling piece 16a can be screwed together with coupling piece 15a while penetrating the membrane 27a. This penetration thus takes place with the help of the sharp component 36a at the front end of the inner plug 37a. The dimensions are preferably chosen so that initially a seal is obtained at the outer opening 22a' of the inner component 22a, before the point 36a penetrates membrane 27a. On the other hand, and as a further safety, a seal is produced at 38a and 39a, respectively, where ring 29a is pressed together.

Figure 5:
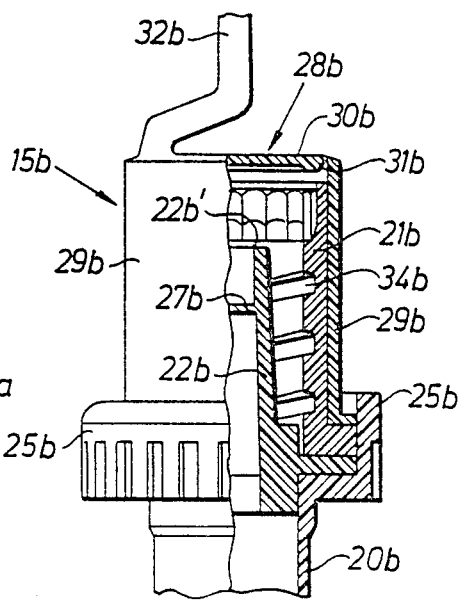
FIG. 5 is a partial, side, elevational, partly sectional view of another coupling member in accordance with the present invention.

Referring next to FIG. 5, a modified embodiment of the coupling member shown in FIG. 2 is set forth. This embodiment includes substantially the same components as those shown in FIG. 2. The same reference designations have thus been used, but the letter a has been replaced by the letter b. The essential difference here is that the outer component 28b has been lengthened so that a cylinder 29b, corresponding to ring 29a, extends down to the emptying nozzle 20b, and is enclosed by the widened outer end 25b of the latter. This outer end is shown on the left side of this figure in its doubled back condition, and in its original condition on the right side thereof. As for the remainder of portion 28b, as in the construction according to FIG. 2, it comprises a pull-ring 32b by means of which the portion 30b can be torn off. The rest of the construction shown in FIG. 5 corresponds substantially to that shown in FIG. 2, and therefore does not require any additional description.

Figure 6:
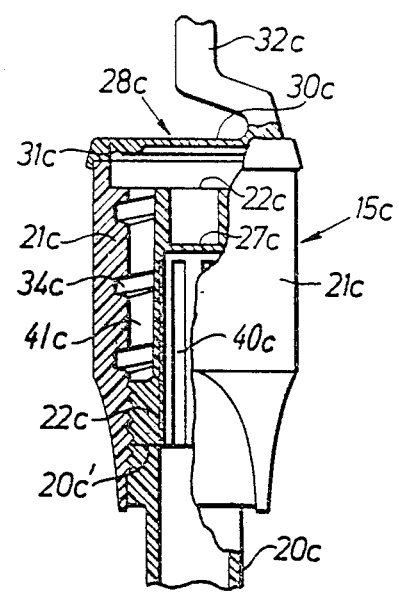
FIG. 6 is a partial, side, elevational, partly sectional view of another coupling member in accordance with the present invention.

Referring next to FIG. 6, a preferred embodiment of the coupling member of this invention is shown. Here again, the same reference numerals have been used, but in this case the letters a and b, respectively, have been replaced by the letter c. In this embodiment, the pipe nozzle 20c is welded to the inner component 22c of the front end 20c of the pipe nozzle 20c. The outer more rigid component 21c together with the welded-on component 28c, has been subsequently forced over the inner component 22c, and the outer end of the pipe nozzle 20c. It will normally be sufficient here to provide a shrinkage fit but, if required, glueing or welding may also be utilized between these components.

As in the constructions according to FIGS. 2 and 5, the top portion 28c is provided with a pull-ring 32c by means of which portion 30c can be removed.

As essential difference between the embodiments described above is in the use of thinner portions, or membrane windows 40c, which are similarly intended to make possible a transfer of steam from the CAPD bag and its emptying nozzle 20c to the space 41c between the components 21c and 22c. By means of this arrangement, effective sterilization of this space in conjunction with the autoclaving is assured.

It will be obvious to those of ordinary skill in this art that a great number of available materials may be used for the different components. For example, the following materials may be suggested: PVC for components 20a, 20b, 20c, 22a, 22b and 22c, polypropylene, polycarbonate or cellulose acetate for components 21a, 21b and 21c; and polypropylene compounded with EVA for components 28a, 28b and 28c. Alternatively, quality PVC may also be chosen for components 28a, 28b and 28c.

It will be understood that the embodiment described herein is merely exemplary and that a person skilled in the art may make many variations and modifications without departing from the spirit and scope of the invention. All such modifications and variations are intended to be included within the scope of the invention as defined in the appended claims.

What is claimed is:

1. A coupling member including a first end, a second end, and a connecting passageway therebetween, said first end of said coupling member being adapted for connection with a mating member connected to a first conduit, and said second end of said coupling member being adapted for connection with a second conduit, whereby said coupling member can be used to couple together said first and second conduits so as to provide for the flow of fluid therebetween, said coupling member comprising an outer substantially cylindrical coupling component which is thermally resistant, and an inner coupling component rigidly affixed to said outer coupling component, said inner coupling component being thinner and more flexible than said outer coupling component and including a substantially cylindrical portion concentrically disposed within said outer coupling component and including an outer surface, an inner surface defining a central passageway, and a penetrable first membrane sealing said central passageway and integral with said cylindrical portion, said cylindrical portion further including a first end corresponding to said first end of said coupling member, and a second end corresponding to said second end of said coupling member, thereby providing an annular space between said outer coupling component and said inner coupling component, with said first end of said inner coupling component being recessed within said first end of said coupling member, whereby said inner coupling component is protected from inadvertent contact thereby, and can withstand autoclaving so that it may be sterilized prior to use and remain substantially sterile thereafter, and said inner coupling component further including a second membrane portion separating said central passageway from said annular space, said second membrane portion being sufficiently thin so that steam can diffuse through said membrane in order to sterilize said annular space between said outer coupling component and said inner coupling component.

2. The coupling member of claim 1, wherein said first end of said coupling member includes a lid member closing said outer coupling component, said lid member including an area of weakness dividing said lid member into a first portion and a second portion, whereby said first portion of said lid member may be readily removed from said coupling member by tearing along said area of weakness so as to expose said first end of said coupling member for mating connection with said mating member.

3. The coupling member of claim 1, wherein said outer surface of said cylindrical portion of said inner coupling component includes a sealing surface defining an inner end of said annular space.

4. The coupling member of claim 1, wherein said outer coupling component and said inner coupling component include peripheral flange means, whereby they may be joined together at said corresponding peripheral flange means.

5. The coupling member of claim 4, wherein both said peripheral flange means of said inner and outer coupling components are disposed substantially perpendicular to the longitudinal axis of said coupling member, and include substantially identical outside diameters.

6. The coupling member of claim 5, wherein both of said peripheral flange means include corresponding planar faces in contact with each other.

7. The coupling member of claim 6, including an outer joining member enclosing the outer diameters of both of said peripheral flange means.

8. The coupling member of claim 1, wherein said outer coupling component is cylindrical and includes an interior threaded portion for threaded engagement with said mating coupling element.

9. The coupling member of claim 1, wherein said penetrable membrane is sufficiently thin so that steam can diffuse through said penetrable membrane during autoclaving.

10. The coupling member of claim 1, wherein said second membrane portion comprises a plurality of second membrane portions.

11. A coupling device comprising a first coupling member and a second coupling member capable of mating with said first coupling member, said first coupling member including a first end, a second end, and a connecting passageway therebetween, and said second coupling member including a first end, a second end, and a connecting passageway therebetween, whereby said coupling device can be used to couple together a pair of conduits so as to provide for the flow of fluid therebetween, said first end of said first coupling member being adapted for connection with said first end of said second coupling member, said first coupling member comprising an outer substantially cylindrical coupling component which is thermally resistant, and an inner coupling component, said inner coupling component being thinner and more flexible than said outer coupling component, and including a substantially cylindrical portion concentrically disposed within said outer coupling component and including an outer surface, an inner surface defining a central passageway, a penetrable membrane closing off said central passageway of said inner coupling component, a first end corresponding to said first end of said first coupling member, and a second end corresponding to said second end of said first coupling member, thereby providing an annular space between said outer coupling component and said inner coupling component, with said first end of said inner coupling component being recessed within said first end of said first coupling member, whereby said inner coupling component is protected from inadvertent contact thereby, and can withstand autoclaving by being supported by said thermally resistant outer coupling component so that it may be sterilized prior to use and remain substantially sterile thereafter, said first end of said second coupling member including a substantially cylindrical penetrating portion including an outer surface and a central passageway therein and being adapted to enter said central passageway of said inner coupling component when said first end of said second coupling member is mated with said first end of said first coupling member so that said outer surface of said penetrating portion sealingly engages said inner surface of said cylindrical portion of said inner coupling component, said penetrating portion of said second coupling member being adapted to sealingly engage said inner flexible coupling component of said first coupling member prior to said penetrating portion of said second coupling member penetrating said membrane, whereby said flow of fluid between said first and second coupling members can take place exclusively within said central passageway of said penetrating portion of said second coupling member and said central passageway of said inner coupling component of said first coupling member and contamination of said central passageway is substantially prevented.

12. The coupling device of claim 11, wherein said second end of said first coupling member is integral with a flexible bag member.

13. The coupling device of claim 11, wherein said outer coupling component and said inner coupling component include peripheral flange means whereby they may be joined together at said corresponding peripheral flange means.

14. The coupling device of claim 13 wherein both of said peripheral flange means of said inner and outer coupling components are disposed substantially perpendicular to the longitudinal axis of said coupling member, and include substantially identical outside diameters.

15. The coupling device of claim 14 wherein both of said peripheral flange means include corresponding planar faces in contact with each other.

16. The coupling device of claim 15 including an outer joining member enclosing the other diameters of both of said peripheral flange means.

17. The coupling device of claim 11, wherein said penetrating portion of said second coupling member includes a first end corresponding to said first end of said second coupling member, and a second end corresponding to said second end of said second coupling member, and wherein said second coupling member includes an outer, substantially cylindrical sheath concentrically disposed surrounding said penetrating portion, thereby providing an annular space between said outer cylindrical sheath and said penetrating portion with said first end of said penetrating portion being recessed within said first end of said second coupling member, whereby said penetrating portion is protected from inadvertent contact thereby, and said outer cylindrical sheath is adapted to enter said annular space between said inner and outer coupling components of said first coupling member when said first end of said second coupling member is mated with the first end of said first coupling member.

18. The coupling device of claim 17 wherein said outer coupling component of said first coupling member includes a threaded inner surface, and said outer cylindrical sheath of said second coupling member includes a correspondingly threaded outer surface, whereby said first and second coupling members may be threadingly engaged with each other therebetween.

19. The coupling device of claim 18, wherein said outer surface of said cylindrical portion of said inner coupling component includes a sealing surface defining an inner end of said annular space between said inner and outer coupling components of said first coupling member, whereby said outer cylindrical sheath is adapted to sealingly contact said sealing surface when said first end of said second coupling member is mated with said first end of said first coupling member.

20. The coupling device of claim 17, including an outer sealing surface projecting from said outer cylindrical sheath of said second coupling member, whereby said outer coupling component of said first coupling member is adapted to sealingly contact said outer sealing surface when said first end of said second coupling member is mated with said first end of said first coupling member.

21. The coupling device of claim 11 wherein said penetrable membrane is sufficiently thin so that steam can diffuse through said penetrable membrane during autoclaving.

22. The coupling device of claim 11 wherein said penetrable membrane comprises a first membrane portion, and wherein said inner coupling component includes a second membrane portion separating said central passageway from said annular space.

23. The coupling device of claim 22 wherein said second membrane portion includes a plurality of second membrane portions.

24. A coupling device comprising a first coupling member and a second coupling member capable of mating with said first coupling member, said first coupling member including a first end, a second end, and a connecting passageway therebetween, and said second coupling member including a first end, a second end, and a connecting passageway therebetween, whereby said coupling device can be used to couple together a pair of conduits so as to provide for the flow of fluid therebetween, said first end of said first coupling member being adapted for connecting with said first end of said second coupling member, said first coupling member comprising an outer substantially cylindrical coupling component and an inner coupling component, said inner coupling component being thin and flexible and not being capable of withstanding autoclaving, and including a substantially cylindrical portion concentrically disposed within said outer coupling component and including an outer surface, an inner surface defining a central passageway, a penetrable membrane closing off said central passageway of said inner coupling component, a first end corresponding to said first end of said first coupling member, and a second end corresponding to said second end of said first coupling member, thereby providing an annular space between said outer coupling component and said inner coupling component, with said first end of said inner coupling component being recessed within said first end of said first coupling member, whereby said inner coupling component is protected from inadvertent contact thereby, and wherein said inner coupling component can withstand autoclaving by being supported by a thermally resistant component made of a more rigid material than said inner coupling component so that it may be sterilized prior to use and remain substantially sterile thereafter, said first end of said second coupling member including a substantially cylindrical penetrating portion including an outer surface and a central passageway therein and being adapted to enter said central passageway of said inner coupling component when said first end of said second coupling member is mated with said first end of said first coupling member so that said outer surface of said penetrating portion sealingly engages said inner surface of said cylindrical portion of said inner coupling component, said penetrating portion of said second coupling member being adapted to sealingly engage said inner flexible coupling component of said first coupling member prior to said penetrating portion of said second coupling member penetrating said membrane, whereby said flow of fluid between said first and second coupling members can take place exclusively within said central passageway of said penetrating portion of said second coupling member and said central passageway of said inner coupling component of said first coupling member and contamination of said central passageway is substantially prevented.

25. The coupling device of claim 24 wherein said outer coupling component comprises said thermally resistant component made of a more rigid material than said inner coupling component and which supports said inner coupling component so that it may be sterilized prior to use and remain substantially sterile thereafter.

26. The coupling device of claim 25 wherein said outer coupling component and said inner coupling component include peripheral flange means whereby they may be joined together at said corresponding peripheral flange means.

27. The coupling device of claim 26 wherein said both of said peripheral flange means of said inner and outer coupling components are disposed substantially perpendicular to the longitudinal axis of said coupling member, and include substantially identical outside diameters.

28. The coupling device of claim 27 wherein both of said peripheral flange means include corresponding planar faces in contact with each other.

29. The coupling device of claim 28 including an outer joining member enclosing the outer diameters of both of said peripheral flange means.

30. The coupling devices of claim 24 wherein said first end of said first coupling member includes an interior threaded portion, and said first end of said second coupling member includes an exterior threaded portion adapted for threaded engagement with said interior threaded portion of said first coupling member.

31. The coupling device of claim 30 wherein said penetrating portion of said second coupling member is recessed with respect to said first end of said second coupling member whereby said penetrating portion is protected from inadvertent contact during use.

32. A coupling device comprising a first coupling member and a second coupling member capable of mating with said first coupling member, said first coupling member including a first end, a second end, and a connecting passageway therebetween, and said second coupling member including a first end, a second end, and a connecting passageway therebetween, whereby said coupling device can be used to couple together a pair of conduits so as to provide for the flow of fluid therebetween, said first end of said first coupling member being adapted for connecting with said first end of said second coupling member, said first coupling member comprising an outer substantially cylindrical coupling component and an inner coupling component, said inner coupling component being thinner and more flexible than said outer coupling component, and including a substantially cylindrical portion concentrically disposed within said outer coupling component and including an outer surface, an inner surface defining a central passageway, a penetrable membrane closing off said central passageway of said inner coupling component, a first end corresponding to said first end of said first coupling member, and a second end corresponding to said second end of said first coupling member, thereby providing an annular space between said outer coupling component and said inner coupling component, with said first end of said inner coupling component being recessed within said first end of said first coupling member, whereby said inner coupling component is protected from inadvertent contact thereby, said first end of said second coupling member including a substantially cylindrical penetrating portion including an outer surface and a central passageway therein and being adapted to enter said central passageway of said inner coupling component when said first end of said second coupling member is mated with said first end of said first coupling member so that said outer surface of said penetrating portion sealingly engages said inner surface of said cylindrical portion of said inner coupling component, said penetrating portion of said second coupling member being adapted to sealingly engage said inner flexible coupling component of said first coupling member prior to said penetrating portion of said second coupling member penetrating said membrane, whereby said flow of fluid between said first and second coupling members can take place exclusively within said central passageway of said penetrating portion of said second coupling member and said central passageway of said inner coupling component of said first coupling member and contamination of said central passageway is substantially prevented.

33. The coupling device of claim 32 wherein said outer coupling component comprises said thermally resistant component made of a more rigid material than said inner coupling component and which supports said inner coupling component so that it may be sterilized prior to use and remain substantially sterile thereafter.

34. The coupling device of claim 33 wherein said outer coupling component and said inner coupling component include peripheral flange means whereby they may be joined together at said corresponding peripheral flange means.

35. The coupling device of claim 34 wherein said both of said peripheral flange means of said inner and outer coupling components are disposed substantially perpendicular to the longitudinal axis of said coupling member, and include substantially identical outside diameters.

36. The coupling device of claim 35 wherein both of said peripheral flange means include corresponding planar faces in contact with each other.

37. The coupling device of claim 36 including an outer joining member enclosing the outer diameters of both of said peripheral flange means.

38. The coupling device of claim 32 wherein said first end of said first coupling member includes an interior threaded portion, and said first end of said second coupling member includes an exterior threaded portion adapted for threaded engagement with said interior threaded portion of said first coupling member.

39. The coupling device of claim 38 wherein said penetrating portion of said second coupling member is recessed with respect to said first end of said second coupling member whereby said penetrating portion is protected from inadvertent contact during use.

* * * * *